United States Patent [19]

Fei et al.

[11] Patent Number: 5,635,387

[45] Date of Patent: Jun. 3, 1997

[54] METHODS AND DEVICE FOR CULTURING HUMAN HEMATOPOIETIC CELLS AND THEIR PRECURSORS

[75] Inventors: Rui G. Fei, Seattle; Shelly Heimfeld, Woodinville; Billy W. Minshall, Mill Creek; Ronald J. Berenson, Mercer Island, all of Wash.

[73] Assignee: CellPro, Inc., Bothell, Wash.

[21] Appl. No.: 415,752

[22] Filed: Apr. 3, 1995

Related U.S. Application Data

[63] Continuation of Ser. No. 11,473, Jan. 25, 1993, abandoned, which is a continuation-in-part of Ser. No. 8,716, Jan. 22, 1993, abandoned, which is a continuation-in-part of Ser. No. 780,488, Oct. 23, 1991, abandoned, which is a continuation-in-part of Ser. No. 513,543, Apr. 23, 1990, abandoned.

[51] Int. Cl.$^6$ ............................. C12N 5/00; C12N 5/02; A61K 35/14
[52] U.S. Cl. .......................... 435/378; 435/384; 435/403; 424/529
[58] Field of Search ................. 435/240.1, 240.2, 435/240.25, 2; 424/529

[56] References Cited

U.S. PATENT DOCUMENTS

| | | | |
|---|---|---|---|
| 3,843,324 | 10/1974 | Edelman et al. | 23/230 B |
| 3,970,518 | 7/1976 | Giaever | 195/1.5 |
| 4,363,634 | 12/1982 | Schall, Jr. | 23/230 B |
| 4,416,777 | 11/1983 | Kuroda et al. | 210/446 |
| 4,714,680 | 12/1987 | Civin et al. | 435/240.25 |
| 4,904,600 | 2/1990 | Ramp | 435/299 |
| 4,965,204 | 10/1990 | Civin | 435/240.27 |
| 5,004,681 | 4/1991 | Boyse et al. | 435/2 |
| 5,087,570 | 2/1992 | Weissman | 435/240.1 |
| 5,162,225 | 11/1992 | Sager et al. | 435/240 |
| 5,192,553 | 3/1993 | Boyse et al. | 424/529 |
| 5,199,942 | 4/1993 | Gillis | 604/4 |
| 5,215,926 | 6/1993 | Etchells, III et al. | 436/501 |
| 5,215,927 | 6/1993 | Berenson et al. | 436/541 |
| 5,225,353 | 7/1993 | Berenson et al. | 436/541 |
| 5,240,856 | 8/1993 | Goffe et al. | 435/299 |
| 5,256,560 | 10/1993 | Lawman et al. | 435/240.25 |
| 5,262,334 | 11/1993 | Berenson et al. | 436/541 |
| 5,397,706 | 3/1995 | Correa et al. | 435/240.31 |
| 5,409,813 | 4/1995 | Schwartz | 435/7.24 |
| 5,409,825 | 4/1995 | Hoffman et al. | 435/240.1 |
| 5,432,054 | 7/1995 | Saunders et al. | 435/2 |
| 5,436,151 | 7/1995 | McGlave et al. | 435/240.1 |
| 5,437,994 | 8/1995 | Emerson et al. | 435/240.2 |
| 5,453,357 | 9/1995 | Hogan | 435/7.21 |
| 5,460,964 | 10/1995 | McGlave et al. | 435/240.21 |
| 5,472,867 | 12/1995 | Kanz et al. | 435/240.25 |

FOREIGN PATENT DOCUMENTS

| | | |
|---|---|---|
| 0 341 966 | 5/1989 | European Pat. Off. |
| 0 451 611 | 3/1991 | European Pat. Off. |
| 0 455 482 | 5/1991 | European Pat. Off. |
| WO87/04628 | 8/1987 | WIPO |
| WO90/15877 | 12/1990 | WIPO |
| WO91/16088 | 10/1991 | WIPO |
| WO91/16452 | 10/1991 | WIPO |
| WO91/16116 | 10/1991 | WIPO |
| WO92/07243 | 4/1992 | WIPO |
| WO92/11355 | 7/1992 | WIPO |
| WO93/08258 | 4/1993 | WIPO |

OTHER PUBLICATIONS

Andreoni et al., "Long-term Culture of Human Bone Marrow. I. Characterization of Adherent Cells in Flow Cytometry," *Exp. Hematol.* 18:431–437, 1990.

Basch et al., "Cell Separation Using Positive Immunoselective Techniques," *Journal of Immunological Methods* 56:269–280, 1983.

Bass and Beckner, "Role of Lymphokines and Cytokines in Bone Marrow Stem Cell Differentiation," *Focus* 12(4):90–95, 1990.

Berenson et al., "Positive selection of viable cell populations using avidin-biotin immunoadsorption," *Journal of Immunological Methods* 91:11–19, 1986.

Beverley et al., "Isolation of human haemotopoietic progenitor cells using monoclonal antibodies," *Nature* 287:332–333, 1980.

Bodine et al., "Effects of Hematopoietic Growth Factors on the Survival of Primitive Stem Cells in Liquid Suspension Culture," *Blood* 78(4):914–920, 1991.

Brandt et al., "Characterization of Human Hematopoietic Stem Cells," *The Biology of Hematopoiesis*, 29–36, 1990.

Brandt et al., "Role of c-kit Ligand in the Expansion of Human Hematopoietic Progenitor Cells," *Blood* 79(3):634–641, 1992.

Brandt et al., "Cytokine-dependent Long-term Culture of Highly Enriched Precursors of Hematopoietic Progenitor Cells from Human Bone Marrow," *J. Clin. Invest.* 86:932–941, 1990.

Briddell et al., "Role of Cytokines in Sustaining Long-Term Human Megakaryocytopoiesis In Vitro," *Blood* 79(2):332–337, 1992.

(List continued on next page.)

*Primary Examiner*—Michael G. Wityshyn
*Assistant Examiner*—Kristin Larson
*Attorney, Agent, or Firm*—Seed and Berry LLP

[57] ABSTRACT

Methods for increasing the number of human hematopoietic precursor cells in vitro are provided. The methods generally comprise (a) separating human hematopoietic precursor cells from mature hematopoietic cells present in a blood product; (b) inoculating the separated precursor cells into a culture vessel containing a culture medium comprising a nutritive medium and a source of growth factors at a density of between $1 \times 10^3$ cells/ml and $4 \times 10^6$ cells/ml; and (c) culturing the cells under conditions and for a time sufficient to increase the number of precursor cells relative to the number of such cells present in the blood product. The culture medium may also include a suitable amount of microcarrier beads. Suitable blood products include bone marrow, umbilical cord blood, and peripheral blood. A device for carrying out such methods is also provided.

28 Claims, 5 Drawing Sheets

OTHER PUBLICATIONS

Broxmeyer et al., "Enhanced Stimulation of Human Bone Marrow Macrophage Colony Formation In Vitro by Recombinant Human Macrophage Colony-Stimulating Factor in Agarose Medium and at Low Oxygen Tension," *Blood* 76(2):323–329, 1990.

Caux et al., "Tumor Necrosis Factor–alpha Strongly Potentiates Interleukin–3 and Granulocyte–Macrophage Colony--Stimulating Factor–Induced Proliferation of Human CD34+Hematopoietic Progenitor Cells," *Blood* 75(12):2292–2298, 1990.

Chabannon and Torok-Storb, "Stem Cell–Stromal Cell Interactions," *Curr. Topics in Microbiol. Immunol.* 177:123–136, 1992.

Dowding et al., "Interferon–α Overrides the Deficient Adhesion of Chronic Myeloid Leukemia Primitive Progenitor Cells to Bone Marrow Stromal Cells," *Blood* 78(2):499–505, 1991.

Eaves et al., "Mechanisms That Regulate the Cell Cycle Status of Very Primitive Hematopoietic Cells in Long–Term Human Marrow Cultures. II. Analysis of Positive and Negative Regulators Produced by Stromal cells Within the Adherent Layer," *Blood* 78(1):110–117, 1991.

Edgington, Stephen, "New Horizons for Stem–Cell Bioreactors," *Bio/Technology* 10:1099–1106, 1992.

Egeland et al., "Myeloid Differentiation of Purified CD34+ Cells After Stimulation With Recombinant Human Granulocyte–Monocyte Colony–Stimulating Factor (CSF), Granulocyte–CSF, Monocyte–CSF, and Interleukin–3," *Blood* 78(12):3192–3199, 1991.

Emerson et al., "The Construction of High Efficiency Human Bone Marrow Tissue Ex Vivo," *Journal of Cellular Biochemistry* 45:268–272, 1991.

Emerson et al., "Developmental Regulation of Erythropoiesis by Hematopoietic Growth Factors: Analysis on Populations of BFU–E From Bone Marrow, Peripheral Blood, and Fetal Liver," *Blood* 74(1):49–55, 1989.

Emerson et al., "Human Recombinant Granulocyte–Macrophage Colony Stimulating Factor and Interleukin 3 Have Overlapping but Distinct Hematopoietic Activities," *J. Clin. Invest.* 82:1282–1287, 1988.

Fibach et al., "Proliferation and Maturation of Human Erythroid Progenitors in Liquid Culture," *Blood* 73(1):100–103, 1989.

Gordon et al., "Plastic–adherent Progenitor Cells in Human Bone Marrow," *Exp. Hematol.* 15:772–778, 1987.

Gordon et al., "An in vitro model for the production of committed haemopoietic progenitor cells stimulated by exposure to single and combined recombinant growth factors," *Bone Marrow Transplantation* 4:353–358, 1989.

Graham et al., "Identification and characterization of an inhibitor of haemopoietic stem cell proliferation," *Nature* 344:442–444, 1990.

Haylock et al., "Ex Vivo Expansion and Maturation of Peripheral Blood CD34+Cells Into the Myeloid Lineage," *Blood* 80(6):1405–1412, 1992.

Heimfeld et al., "The in vitro response of phenotypically defined mouse stem cells and myeloerythroid progenitors to single or multiple growth factors," *Proc. Natl. Acad. Sci. USA* 88:9902–9906, 1992.

Heimfeld & Weissman, "Characterization of Several Classes of Mouse Hematopoietic Progenitor Cells," *Current Topics in Microbio. & Immunol.* 177:95–105, 1992.

Heimfeld & Weissman, "Development of Mouse Hematopoietic Lineages," *Current Topics in Developmental Biology* 25:155–175, 1991.

Iscove et al., "A Soluble Activity From Adherent Marrow Cells Cooperates With IL 3 in Stimulating Growth of Pluripotential Hematopoietic Precursors," *Blood* 71(4):953–957, 1988.

Jackson et al., "Megakaryocytopoiesis and Platelet Production Are Stimulated During Late Pregnancy and Early Postpartum in the Rat," *Blood* 79(7):1672–1678, 1992.

Kobayashi et al., "Synergistic Effects of Interleukin–1β and Interleukin–3 on the Expansion of Human Hematopoietic Progenitor Cells in Liquid Cultures," *Blood* 78(8):1947–1953, 1991.

Koller et al., "Effects of Synergistic Cytokine Combinations, Low Oxygen, and Irradiated Stroma on the Expansion of Human Cord Blood Progenitors," *Blood* 80(2):403–411, 1992.

Kumar & Lykke, "Cell Separation: A Review," *Pathology* 16:53–62, 1984.

Lakow and Basch, "Positive Immunoselection Using Antibody–Enzyme Complexes," *Journal of Immunological Methods* 44:135–151, 1981.

Lasky and Bhatia, "Future Applications of Marrow Progenitor Growth," in Sacher et al., ed., *Processsing of Bone Marrow for Transplantation*, 1990, pp. 83–99.

Lawman, et al., "Ex Vivo Expansion and Differentiation of Hematopoietic Stem Cells," *Journal of Hematotherapy* 1:251–259, 1992.

Lemoli et al., "Proliferation of hematopoietic progenitors does not require feeder–layer formation in human long–term bone marrow cultures in gas permeable plastic bags & it is enhanced by colony–stimulating factors," Paper presented in part @ ASH/ISH Meeting, Boston, Nov. 28–Dec. 4, 1990.

Lemoli et al., "Proliferation of Hematopoietic Progenitors is Enhanced by Addition of Exogenous Colony Stimulating Factors (CSFs) in Human Long–Term Bone Marrow Cultures (LTBMC) in Absence of Feeder–Layer Formation," ISEH Abstract, 1991.

McNiece et al., "Recombinant Human Stem Cell Factor Synergises with GM–CSF, G–CSF, IL–3 and Epo to Stimulate Human Progenitor Cells of the Myeloid and Erythroid Lineages," *Exp. Hematol.* 19:226–231, 1991.

McNiece et al., "Detection of a Human CFC With a High Proliferative Potential," *Blood* 74(2):609–612, 1989.

Monette & Sigounas, "Some Observations on the Growth Requirements of Multi–Potent Stem Cells Under Defined Cultured Conditions," *The Biology of Hematopoiesis*, 1990, pp. 37–48.

Moore, Malcolm, "Clinical Implications of Positive and Negative Hematopoietic Stem Cell Regulators," *Blood* 78(1);1–19, 1991.

Moore, Malcolm, "The Future of Cytokine Combination Therapy,"*Cancer* 67(10):2718–2726, 1991.

Musashi et al., "Synergestic Interactions Between Interleukin–11 and Interleukin–4 in Support of Proliferation of Primitive Hematopoietic Progenitors of Mice," *Blood* 78(6):1448–1451, 1991.

Naughton et al., "A Three–Dimensional Culture System for the Growth of Hematopoietic Cells," *Bone Marrow Purging & Processing*, 1990, pp. 435–445.

Quesenberry, P.J., "Hematopoietic Cells in Dexter Culture," *Current Topics in Microbiol. and Immunol.* 177:152–166, 1992.

Quesenberry et al., "Long-Term Marrow Cultures: Human and Murine Systems," *Journal of Cellular Biochemistry* 45:273–278, 1991.

Saeland et al., "Combined and Sequential Effects of Human IL-3 and GM-CSF on the Proliferation of CD34+Hematopoietic Cells From Cord Blood," *Blood* 73(5):1195–1201, 1989.

Sato et al., "Purification of Human Marrow Progenitor Cells and Demonstration of the Direct Action of Macrophage Colony–Stimulating Factor on Colony–Forming Unit–Macrophage," *Blood* 78(4):967–974, 1991.

Schwartz et al., "In Vitro Myleopoiesis Stimulated by Rapid Medium Exchange and Supplementation With Hematopoietic Growth Factors," *Blood* 78(12):3155–3161, 1991.

Sieff et al., "Dependence of Highly Enriched Human Bone Marrow Progenitors on Hemopoietic Growth Factors and Their Response to Recombinant Erythropoietin," *J. Clin. Invest.* 77:74–81, 1986.

Sonoda et al., "Analysis in serum–free culture of the targets of recombinant human hemopoietic growth factors: Interleukin 3 and granulocyte/macrophage–colony–stimulating factor are specific for early developmental stages," *Proc. Natl. Acad. Sci. USA* 85:4360–4364, 1988.

Spangrude, et al., "Mouse Hematopoietic Stem Cells," *Blood* 78(6):1395–1402, 1991.

Sutherland et al., "Functional characterization of individual human hematopoietic stem cells cultured at limiting dilution on supportive marrow stromal layers," *Proc. Natl. Acad. Sci. USA* 87:3584–3588, 1990.

Sutherland et al., "Characterization and Partial Purification of Human Marrow Cells Capable of Initiating Long–Term Hematopoiesis In Vitro," *Blood* 74(5):1563–1570, 1989.

Takaue et al., "Effects of Recombinant Human G-CSF, GM-CSF, IL-3, and IL-1α on the Growth of Purified Human Peripheral Blood Progenitors," *Blood* 76(2):330–335, 1990.

Tavassoli et al., "The Watchmaker's Dilemma: Building a Tower of Microenvironments in vitro," *Exp. Hematol.* 20:286–287, 1992.

Udomsakdi et al., "Separation of Functionally Distinct Subpopulations of Primitive Human Hematopoietic Cells using Rhodamine–123," *Exp. Hematol.* 19:338–342, 1991.

Van de Rijn et al., "Mouse hematopoietic stem–cell antigen Sca–1 is a member of the Ly–6 antigen family," *Proc. Natl. Acad. Sci. USA* 86:4634–4638, 1989.

Verfaillie, Catherine, "Direct Contact Between Human Primitive Hematopoietic Progenitors and Bone Marrow Stroma Is Not Required for Long–term In Vitro Hematopoiesis," *Blood* 79(11):2821–2826, 1992.

Weilbaecher, et al., "Culture of Phenotypically Defined Hematopoietic Stem Cells and Other Progenitors at Limiting Dilution on Dexter Monolayers," *Blood* 78(4):945–952, 1991.

Wessels et al., "Two Distinct Loci on the Short Arm of Chromosome 16 Are Involved in Myeloid Leukemia," *Blood* 77(7):1555–1559, 1991.

Wysocki et al., "Panning for lymphocytes: A method for cell selection," *Proc. Natl. Acad. Sci. USA* 75:2844–2848, 1978.

Zipori, Dov, "Regulation of Hemopoiesis by Cytokines that Restrict Options for Growth and Differentiation," *Cancer Cells* 2(7):205–211, 1990.

Smith et al., "Brit. J. of Haematology." vol. 63, pp. 29–34, 1986.

Visser, et al., "J. Exp. Med." vol. 59, Jun. 1984, pp. 1576–1590.

de Vries et al., "J. Exp. Med.," vol. 173, May 1991, pp. 1205–1211.

Zsebo, et al., "Cell," vol. 63, Oct. 5, 1990, pp. 195–201.

METHODS AND DEVICE FOR CULTURING HUMAN HEMATOPOIETIC CELLS AND THEIR PRECURSORS

CROSS-REFERENCE TO RELATED APPLICATION

This application is a continuation of U.S. patent application Ser. No. 08/011,473, filed Jan. 25, 1993, now abandoned; which was a continuation-in-part of U.S. patent application Ser. No. 08/008,716, filed Jan. 22, 1993, now abandoned; which was a continuation-in-part of U.S. patent application Ser. No. 07/780,488, filed Oct. 23, 1991, now abandoned; which was a continuation-in-part of U.S. patent application Ser. No. 07/513,543, filed Apr. 23, 1990, now abandoned.

TECHNICAL FIELD

The present invention relates generally to hematopoietic (blood-forming) cells and, more specifically, to methods and devices for culturing human hematopoietic cells and their precursors in vitro.

BACKGROUND OF THE INVENTION

Cancer accounts for over one-fifth of the total mortality in the United States, making it the second leading cause of death. The leading types of cancer are lung, prostate (men), colorectal, and breast (women). Currently, most cancers are treated by surgery, chemotherapy, radiation therapy, or a combination of the above.

A disadvantage of chemotherapy and radiation therapy is that, in addition to destroying the cancer, they also destroy or suppress the main blood-forming organ in the body, the bone marrow, resulting in reduced blood-clotting and infection-fighting capability in the patient. The phenomena of marrow damage or destruction are referred to, respectively, as myelosuppression or myeloablation.

Hematopoietic cells arise in the bone marrow from a totipotent stem cell which is characterized as being able to renew itself as well as to give rise to cells of all the other hematopoietic lineages, including the erythroid, megakaryocytic, myeloid, and lymphoid lineages. This stem cell gives rise to progenitor cells, for example, erythroid progenitors and myeloid progenitors, which are committed to differentiate along a specific lineage. Progenitor cells, in turn, give rise to differentiated cells which are morphologically recognizable as belonging to a certain lineage and which have a limited or no capacity to proliferate. In humans, stem cells and progenitor cells express the CD34 antigen, while more differentiated hematopoietic cells do not.

To avoid the above-mentioned problem of myelosuppression, cancer therapy is often given in divided doses, which allows the bone marrow to recover between treatment cycles. Unfortunately, this method of treatment allows the cancer to grow back and to develop resistance to the chemotherapeutic agents being used to treat it. Use of higher doses of chemotherapy or radiation therapy is expected to result in higher cure rates among cancer patients, but may destroy the bone marrow completely (myeloablation), necessitating that the patient be transplanted with bone marrow from a histocompatible donor (an allogeneic transplant) or with his own marrow (an autologous transplant), harvested prior to myeloablative treatment.

The ability to culture hematopoietic cells and their precursors, derived from the bone marrow, peripheral blood, or umbilical cord blood of the patient or a suitable donor, offers the potential to overcome the disadvantages of high-dose cancer therapy by providing an expanding source of cells which can be used to reconstitute the patient's blood-clotting and infection-fighting functions between cycles of therapy. In addition, the ability to expand hematopoietic cells and their precursors in vitro may relieve dependence on bone marrow aspiration or multiple aphereses as the only means of obtaining sufficient cells for transplantation.

It is generally believed in the art that in vitro growth of hematopoietic cells and their precursors requires both the appropriate growth factors (cytokines), or combination thereof, and the presence of bone marrow stromal cells. The latter are believed to be particularly important and are thought to function both as sites of attachment for developing hematopoietic cells and as sources of as yet unidentified growth factors required by the cells for proliferation and differentiation. In the absence of stromal elements, it is believed that hematopoietic precursor cells do not expand in number.

Early work in the field of hematopoietic stem cell culture centered around the culture of bone marrow aspirates from mouse in agar gel or liquid medium. Unfractionated bone marrow (including stem cells, progenitor cells, more differentiated hematopoietic cells, and stromal elements) was used to inoculate these cultures, which were generally short-lived and resulted in little or no increase in cell number, particularly in the stem cell and progenitor compartments. The results were even less promising when human bone marrow was employed. The cells were generally observed to adhere to the bottom and sides of the vessel in which they were cultured and their removal therefrom was difficult.

Subsequent efforts focused on inoculating whole bone marrow, again mouse, onto pre-established monolayers of bone marrow stromal cells (so-called Dexter cultures; Dexter, *Acta Haematol.* 62: 299–305, 1979). While some success was obtained in the mouse with Dexter cultures, the same approach was disappointing in the human. Various investigators have observed a steady decline in the numbers of all cell types in human Dexter cultures (reviewed in Quesenberry, Curr. Topics in *Microbiol. Immunol.* 177: 151, 1992).

A further disadvantage of Dexter cultures is that, to the extent that there is expansion of hematopoietic precursor cells, these cells adhere to the stromal layer and are extremely difficult to recover from the culture without employing conditions which damage the cells. The proliferating cells which are released into the culture medium (that is, the non-adherent cells) are generally more mature cells, which cannot restore sustained hematopoiesis in a transplanted individual.

Several investigators have attempted to improve upon the Dexter culture. For example, Naughton et al. describe the establishment of the stromal cell layer on a nylon screen (Bone Marrow Purging and Processing, Alan R. Liss (pub.), pg. 435–445, 1990). Emerson et al. have used a protein matrix, such as collagen-coated beads or membranes, to support the stromal cell layer (WO90/15877, published Dec. 27, 1990 and WO92/11355, published Jul. 9, 1992). Neither of these methods, however, overcomes the disadvantage mentioned above, namely, that hematopoietic precursor cells adhere to the stromal layer, from which they are not easily removed.

There remains a need in the art for a method of culturing human hematopoietic cells, which method (a) is independent of the presence of bone marrow stromal elements; (b) results in expansion of the number of hematopoietic precursor cells; and (c) enhances the yield and recovery of the precursor cells without compromising viability. The present invention fulfills this need and further provides other related advantages.

SUMMARY OF THE INVENTION

Briefly stated, the present invention provides methods for increasing the number of human hematopoietic precursor cells in vitro. More specifically, within a primary aspect of the present invention, the method comprises (a) separating human hematopoietic precursor cells from mature hematopoietic cells present in a blood product; (b) inoculating the separated precursor cells into a culture vessel containing a culture medium comprising a nutritive medium and a source of growth factors, and, optionally, microcarrier beads, at an initial density of between $1 \times 10^3$ cells/ml and $4 \times 10^6$ cells/ml; and (c) culturing the cells under conditions and for a time sufficient to increase the number of precursor cells relative to the number of such cells present in the blood product.

Within one embodiment of the primary aspect of the invention, the step of separating is by immunoselection based upon the presence of CD34 antigen expressed by the precursor cells. More specifically, within this embodiment, the method comprises (a) separating CD34-positive cells from CD34-negative cells within a blood product; (b) inoculating the separated CD34-positive cells into a culture vessel containing a culture medium comprising a nutritive medium and a source of growth factors at an initial cell density of between $1 \times 10^3$ cells/ml and $1 \times 10^4$ cells/ml, optionally containing a source of plasma or serum and, the culture medium optionally, microcarrier beads; and (c) culturing the cells for a time sufficient to increase the number of CD34-positive cells relative to the number of CD34$^+$ such cells present in the blood product. Within a related embodiment, subsequent to the step of separating CD34-positive from CD34-negative cells, the method comprises further separating the CD34-positive cells into HLA-DR-positive and HLA-DR-negative populations.

Within one aspect of the present invention, a method is provided for culturing human hematopoietic precursor cells in vitro, comprising (a) separating CD34-positive cells from CD34-negative cells present in bone marrow, peripheral blood, or umbilical cord blood; (b) inoculating the separated CD34-positive cells into a stirred culture vessel containing a nutritive medium, a source of growth factors, and optionally containing a source of plasma; and (c) culturing the cells for at least about 4 days.

Within another aspect of the present invention, a device is provided for culturing human hematopoietic precursor cells within suspension in vitro, comprising (a) a means for separating target cells from non-target cells in a blood product, such as a bone marrow, peripheral blood, or umbilical cord blood specimen; (b) a means for culturing the separated target cells; (c) sensor means for providing signals indicative of the optical densities of fluids flowing out of the separating means and into the culturing means, and out of the culturing means and into a collection means; (d) valve means responsive to valve control signals for selectively enabling fluid coming out of the separating means to flow into the culturing means, and fluid coming out of the culturing means to flow into the collection means; and (e) data processing means for controlling operation of the separating means and the culturing means.

These and other aspects will become evident upon reference to the following detailed description and attached drawings.

BRIEF DESCRIPTION OF THE DRAWINGS

FIG. 4, Block B is a graph depicting the effect of different human plasma concentrations on expansion of CFU-GM and cell numbers. Data are the mean ±1 SEM from two experiments at cell concentrations of $6 \times 10^4$/ml and $4 \times 10^5$/ml, respectively. P value between 1% and 5% plasma group both in expansion of cell and CFU-GM numbers are <0.05, while above 5% plasma groups, all P values are >0.2.

DETAILED DESCRIPTION OF THE INVENTION

The present invention provides methods for increasing the number of human hematopoietic precursor cells in vitro. Briefly, human hematopoietic precursor cells are separated from a blood product, such as bone marrow, peripheral blood, or umbilical cord blood of a patient or donor. As discussed in more detail below, such separation may be performed, for example, by immunoselection on the basis of their expression of an antigen, such as the CD34 antigen, which is present on substantially all hematopoietic precursor cells, but is substantially absent from more mature hematopoietic cells. The separated hematopoietic precursor cells are then inoculated into a suitable vessel containing a culture medium comprising a nutritive medium supplemented with a source of growth factors and, optionally, human or other animal plasma or serum. The culture medium may also optionally include microcarrier beads to which the cells are capable of attaching. The resultant cell suspension is cultured under conditions and for a time sufficient to increase the number of hematopoietic precursor cells relative to the number of such cells present in the blood product. The cells may then be separated by any of a variety of methods, such as centrifugation or filtration, from the medium in which they have been cultured, and may be washed one or more times with fresh medium or buffer. Optionally, the cells may be re-separated into CD34-positive and -negative fractions, prior to resuspension to a desired concentration in a medium or buffer suitable for infusion. The cells may then be infused into a patient.

Surprisingly, separated precursor cells, such as CD34-positive cells, will expand in number when cultured in the absence of bone marrow stromal elements, enabling clinically practicable expansion and recovery of hematopoietic precursor cells. By working with separated precursor cells, the volumes of cells and culture fluids which must be handled are reduced to more manageable numbers. Further, a high degree of expansion can be achieved when one starts with separated CD34-positive cells, rather than with an unseparated blood product. This is believed to be due to the removal of cells otherwise present in the blood product, which inhibit expansion of the precursor cells. Under the conditions employed in the methods of this invention, cell recovery is greatly facilitated and viability is preserved. Most importantly, the yield of hematopoietic precursor cells, capable of mediating long-term hematopoietic recovery in a myelosuppressed or myeloablated host, is increased.

The ability to expand hematopoietic precursor cells in vitro by the methods of the present invention is expected to have tremendously important consequences for cancer treatment, enabling the administration of chemotherapy in doses which would previously have been considered life-threatening. Currently, damage to the bone marrow is the major dose-limiting side effect of chemotherapy. However, using the instant methods, hematopoietic precursor cell support can be provided to patients receiving high-dose chemotherapy which, in turn, is expected to improve patient survival in many types of cancer.

Cell Separation

Within the context of the present invention, hematopoietic precursor cells include those cells which express the CD34 antigen, among other surface antigens, and include totipotent stem cells as well as committed progenitor cells. The level of expression of the CD34 antigen will vary from one cell type to another. Consequently, a cell is operationally defined as CD34-positive if it expresses sufficient CD34 antigen to be detected by a given method of assay. For example, CD34-positive cells can be identified by flow microfluorimetry using a fluorescence-activated cell sorter (FACS), by immunofluorescence or immunoperoxidase staining using a fluorescence or light microscope, by radioimmunoassay, or by immunoaffinity chromatography, among numerous other methods which will be readily apparent to one skilled in the art (see, for example, Lansdorp and Thomas in Bone Marrow Processing and Purging, A. P. Gee (ed.), Boca Raton: CRC Press (1991) pg. 351). Hematopoietic precursor cells can also be detected by various colony-forming assays, such as CFU-GM and CFU-S assays (see, for example, Sutherland et al., in Bone Marrow Processing and Purging, A. P. Gee (ed.), Boca Raton: CRC Press (1991), pg. 155).

Hematopoietic precursor cells, including CD34-positive cells, may be obtained from any of a variety of blood products, including bone marrow, peripheral blood, umbilical cord blood, fetal liver, and spleen. Bone marrow is a particularly rich source of precursor cells (1–2% of marrow), but alternate sources may be preferable because of the discomfort associated with bone marrow aspiration. Bone marrow is typically aspirated from the iliac crest, but may be obtained from other sites (such as the sternum) if necessitated by prior or concurrent disease or therapy.

Peripheral blood contains fewer precursor cells (typically <1% of peripheral blood mononuclear cells), but is generally easier to obtain than bone marrow. The number of precursor cells circulating in peripheral blood can be increased by prior exposure of the donor to certain growth factors, such as G-CSF or SCF, and/or certain drugs, such as 5-fluorouracil (reviewed in Korbling and Martin, Plasma Ther. Transfer Technol. 9:119, 1980). Peripheral blood collected from patients or donors who have been pre-treated to increase the number of circulating CD34-positive cells is referred to as having been "mobilized." Depending upon the volume which is desired, blood may be obtained by venipuncture or by one or more aphereses.

Precursor cells can also be obtained from umbilical cord blood at the time of delivery, either by simple gravity-induced drainage or manual expression (see Boyse et at., U.S. Pat. No. 5,004,681, issued Apr. 2, 1991, herein incorporated by reference).

Although one can readily separate a bone marrow or peripheral blood specimen or apheresis product into precursor and mature cells, (such as CD34-positive and CD34-negative populations), it is generally preferred to prepare a buffy coat or mononuclear cell fraction from these specimens first, prior to separation into the respective populations. Methods for the preparation of buffy coats and mononuclear cell fractions are well-known in the art (Kumar and Lykke, Pathology 16: 53, 1984).

Separation of precursor cells from more mature cells can be accomplished by any of a variety of methods known to those skilled in the art, including immunoaffinity chromatography (Basch et al., J. Immunol. Methods 56: 269, 1983), fluorescence-activated cell sorting, panning (Wysocki and Sato, Proc. Natl. Acad. Sci. (USA) 75: 2844, 1978), magnetic-activated cell sorting (Miltenyi et al., Cytometry 11:231, 1990), and cytolysis. Generally, separation of a heterogeneous population of cells, such as in a bone marrow aspirate or a peripheral blood specimen or apheresis product, into target (such as, CD34-positive) and non-target (such as, CD34-negative) fractions is rarely complete. For the purposes of the present invention, separation is considered to have been accomplished if the target fraction is comprised of at least about 20% precursor cells, more often about 50% precursor cells, and preferably about 70% precursor cells. In addition, it may be desirable to keep the total numbers of mature hematopoietic cells, such as platelets, granulocytes, and red cells, as low as possible in order to prevent clumping and the release of degradative enzymes which can adversely affect the recovery and viability of engrafting cells. More specifically, it may be desirable that the target fraction be comprised of less than about 5% platelets, 50% granulocytes, and 10% red cells and, preferably, less than about 1% platelets, 25% granulocytes, and 1% red cells.

Precursor cells may be positively selected or negatively selected. By positive selection is meant the capture of cells by some means, usually immunological, on the basis of their expression of a specific characteristic or set of characteristics (usually an antigen(s) expressed at the cell surface). For example, CD34-positive cells can be positively selected by any of the above methods (except cytolysis, which would result in destruction of the desired cells) on the basis of their expression of the CD34 antigen utilizing an anti-CD34 antibody, such as the monoclonal antibodies 12.8, My-10 (commercially available from Becton Dickinson Co., Mountain View, Calif.), or Q-Bend 10 (commercially available from Biosystems Ltd., Waterbeach, Cambridge, England).

Negative selection means the exclusion or depletion of cells by some means, usually immunological, on the basis of their lack of expression of a specific characteristic or set of characteristics (again, usually a surface antigen). For example, CD34-positive cells can be negatively selected by any of the above methods on the basis of their lack of expression of lineage-defining antigens, such as CD 19 (for B lymphocytes), CD3 (for T lymphocytes), CD56 (for NK cells), etc., utilizing antibodies to the above-mentioned and other lineage-defining antigens. By using a cocktail or mixture of monoclonal antibodies directed to red cell, platelet, granulocyte, lymphocyte and/or tumor cell antigens, it is possible to leave behind a population of cells which is highly enriched for CD34-positive cells. Numerous monoclonal and polyclonal antibodies suitable for this purpose are known in the art (see Leukocyte Typing IV, Knopp et al. (eds.), Oxford UP, 1989) and are commercially available from a wide variety of sources (for example, Becton Dickinson Co., Mountain View, Calif.; Coulter Immunology, Hialeah, Fla.; Ortho Diagnostics, Raritan, N.J., etc.).

Alternatively, precursor cells can be separated from mature cells by a combination of negative and positive selection techniques. A preferred combination of negative and positive selection techniques is comprised of a first selection for CD34-positive cells utilizing an anti-CD34 antibody, followed by a second selection for HLA-DR-negative/CD34-positive cells, using an anti-HLA-DR antibody to a non-polymorphic determinant on the DR molecule. Antibodies to non-polymorphic determinants on the HLA-DR molecules are well-known in the literature (see Knopp et al., op. cit.) and are available from a variety of sources, including those mentioned above. An example of a suitable monoclonal anti-HLA-DR antibody is the antibody produced by hybridoma cell line L243 (Lampson et al., *J. Immunol.* 125: 293, 1980), which cell line is available from the American Type Culture Collection (Rockville, Md.) under the designation ATCC HB55. The advantage of this or other dual selection strategies is that the volume of cells which is placed into culture is smaller and thus more manageable.

Although selection of CD34-positive cells usually involves the use of one or more antibodies or fragments thereof, in some cases selection may involve the use of lectins or other types of receptors or ligands expressed on the cell surface. Among other antibodies, antigens, receptors and ligands which may be useful, alone or in combination with other markers, for separating CD34-positive cells from CD34-negative cells are transferrin, the transferrin receptor, soybean agglutinin, c-kit ligand, c-kit receptor, HLA-DR, CD33, etc.

Within another aspect of the invention, the precursor cells are periodically separated from more mature cells. Briefly, mature cells (which include not only terminally differentiated blood cells, but cells of an intermediate lineage) are believed to inhibit the expansion and differentiation of precursor cells via a feedback control mechanism. Removal of more mature cells from a culture thus permits expansion of the precursor cells to many times their original numbers. Within the context of the present invention, periodically separating means removal of mature cells at least every 7 days, preferably every 4 days.

Various methods may be utilized in order to periodically separate precursor cells. For example, within one embodiment, cells are separated on an affinity column, incubated in a selected medium, and then subsequently reseparated in order to separate the precursor cells from the newly differentiated mature cells.

Particularly preferred methods and devices for the selection of precursor cells, such as CD34-positive cells, are described in co-pending U.S. applications Ser. No. 07/769,529 and 07/769,530, both filed Oct. 3, 1991; Ser. No. 07/739,911, filed Aug. 2, 1991; and Ser. No. 780,750, filed Oct. 23, 1991 (all of which are herein incorporated by reference in their entirety). Briefly, these applications describe methods and devices for isolating or separating target cells, such as hematopoietic precursor cells, from a mixture of non-target and target cells, wherein the target cells are labeled, directly, or indirectly, with a biotinylated antibody to a target cell surface antigen. Labeled cells are separated from unlabeled cells by flowing them through a bed of immobilized avidin, the labeled cells binding to the avidin by virtue of the biotinylated antibody bound to their surface, while the unlabeled cells pass through the bed. After washing the bed material, the labeled (bound) cells can be eluted from the bed, for example, by mechanical agitation. A cell separator device is also provided for separating target cells from non-target cells, comprising (a) a column assembly which includes a column, a sample fluid supply bag and a fluid collection bag wherein the column is provided for receiving the sample fluid from the sample fluid supply bag and for separating the target cells from the sample fluid and retaining the target cells, and wherein the fluid collection bag is provided for receiving the target cells after being released from the column, (b) an agitation means for agitating the contents of the column to assist in releasing the sample cells retained in the column, the agitation means being responsive to a drive signal for varying amounts of agitation of the contents of the column to vary the rate at which the sample cells are released, (c) a column sensor means for providing a column signal indicative of the optical density of fluid flowing out of the column and into the fluid collection bag, (d) a column valve means responsive to a column valve control signal for selectively enabling the fluid coming out of the column to flow into the fluid collection bag, and (e) a data processor means for controlling the operation of the cell separator, the data processor means being responsive to the column signal for providing the drive signal and the column valve control signal to prevent inadequate concentrations of the target cells from being collected. One embodiment of this invention is the CEPRATE SC™ cell separation system described in Berenson et al. (*Adv. Bone Marrow Purging & Processing*, N.Y.: Wiley-Liss, 1992, pg. 449).

Nutritive Media

Subsequent to separation, precursor cells are inoculated into a culture medium comprised of a nutritive medium, any number of which, such as RPMI, TC 199, X-VIVO-10, or Iscove's DMEM, along with a source of growth factors, will be apparent to one skilled in the art. Proliferation and differentiation of precursor cells may be enhanced by the addition of various components to the medium, including a source of plasma or serum. Among sources of plasma or serum are fetal bovine and human. Particularly preferred are human autologous plasma or human AB⁻ plasma which have been screened in accordance with standard blood bank procedures to ensure the absence of infectious agents, such as HBV or HIV. The amount of plasma or serum which is used will vary, but is usually between 5 and 50% (by volume) of the medium in which the cells are grown, and more often between 5 and 25%.

Growth Factors

Among growth factors which may be advantageously employed in the culture medium are interleukins (Il) 1–15, erythropoietin (EPO), stem cell factor (SCF, also known as mast cell growth factor and c-kit ligand), granulocyte-colony stimulating factor (G-CSF), granulocyte, macrophage-colony stimulating factor (GM-CSF), macrophage-colony stimulating factor (M-CSF), tumor growth factor beta (TGF beta), tumor necrosis factor alpha (TNF alpha), the interferons (IFN alpha, beta, or gamma), fibroblast growth factor (FGF), platelet-derived growth factor (PDGF), insulin-like growth factors (IGF-1 and IGF-2), etc. Growth factors are commercially available, for example, from R&D Systems (Minneapolis, Minn.). Particularly preferred are combinations of growth factors, especially the combination of SCF, Il-1 alpha, Il-3 and Il-6.

In general, the above-mentioned growth factors are purified or partially purified before they are added to the culture medium. Usually, they will be produced by recombinant DNA methods, but they may also be purified by standard biochemical techniques from conditioned media. Non-naturally-occurring growth factors can also be produced by recombinant DNA methods, for example, PIXY 321 is a fusion protein which has both GM-CSF and Il-3 activity. It will be evident to those skilled in the art that other fusion proteins, combining multiple growth factor activities, can be readily constructed, for example, fusion proteins combining SCF activity with that of other growth factors such as Il-1, Il-3, Il-6, G-CSF, and/or GM-CSF.

The amount of each growth factor to be used is determined empirically and will vary depending on the purity and method of production of the factors. Generally, concentrations between 0.5 and 100 ng/ml are sufficient, more often between 0.5 and 50 ng/ml. Where more than one growth factor is used, the optimum amount of each factor should be determined in combination with the other factors to be used. This is because some growth factors can modulate the activity of other growth factors, necessitating that they be used sequentially rather than simultaneously, while in other instances, growth factors may act synergistically. Still other growth factors may enhance proliferation or differentiation along one pathway, while suppressing another pathway of interest.

Conditioned Medium

Alternatively, separated precursor cells may be cultured in a nutritive medium, optionally containing a source of plasma or serum, which medium has been previously conditioned by exposure to cells for a variable period of time and under conditions sufficient to allow those cells to secrete products, such as growth factors, into the medium. For example, conditioned medium suitable for the culture of separated CD34-positive cells may be prepared by inoculating an SV40-transformed stromal cell line (Nemunaitis et at., *J. Clin. Invest.* 83: 593, 1989) or a T-lymphocyte line (such as Mo, Molt-4, CEM, etc.) into a nutrient medium (optionally containing plasma or serum), allowing the cells to grow, usually for 1 to 3 days, and then separating the cells from the medium (for example, by centrifugation or filtration). Optionally, the conditioned medium may be sterilized and/or concentrated prior to use and/or supplemented by the addition of exogenous growth factors.

Although stromal cell lines are particularly preferred for generating conditioned medium, it will be apparent to those skilled in the art that numerous other cell lines have been described in the literature which secrete a variety of growth factors and which may be utilized to condition medium. In addition, it will be apparent that multiple cell lines may be inoculated simultaneously in order to produce medium conditioned by more than one line. Alternatively, different batches of medium can be conditioned by different cell lines and the batches combined, after the cells have been separated and discarded, to achieve the same effect. Although it is preferred to utilize established cell lines for conditioning medium, it will be apparent to those skilled in the art that primary cell lines can also be employed for this purpose.

The length of time for which medium is conditioned may vary from 1 day to 2 weeks, but will usually be between 1 day and 1 week and more often, between 1 day and 5 days. In addition to conditioning the medium by exposing it to cells, such as stromal cells or lymphocytes, the medium may also be supplemented by the addition of one or more purified or partially purified growth factors, such as those mentioned above. The term "conditioned medium" is used to include medium conditioned solely by exposure to cells as well as medium conditioned by exposure to cells and supplemented with exogenous growth factors.

Conditioned medium may be prepared with or without a source of serum or plasma. If used, the serum or plasma may be of human or other animal origin. Particularly preferred is human autologous plasma or human AB⁻ plasma which has been screened in accordance with standard blood bank procedures to ensure the absence of infectious agents. The amount of plasma or serum which is used will vary, but is usually between 5 and 50% (by volume) of the medium in which the cells are grown, and more often between 5 and 25%.

Conditioned medium may be concentrated prior to use, for example, by ultrafiltration. The amount of concentration will vary, but is usually between 2 and 100-fold, more often between 2 and 50-fold, and most often between 2 and 10-fold. Separated precursor cells may be inoculated directly into conditioned medium (concentrated or non-concentrated) or they may be inoculated into a mixture of conditioned (concentrated or non-concentrated) and non-conditioned medium (with or without exogenously supplied growth factors and serum or plasma). If inoculated into a mixture of conditioned and non-conditioned medium, the ratio of conditioned (non-concentrated) to non-conditioned medium will usually be between 1:1 and 1:10 (on a volume basis), more often between 1:1 and 1:5, and most often between 1:1 and 1:2. Although these ratios are expressed for non-concentrated conditioned medium, it will be apparent to those skilled in the art that the equivalent ratios can be obtained using smaller volumes of concentrated conditioned medium.

Culture Vessels

Separated precursor cells may be cultured in any vessel which is capable of being sterilized, is adapted or adaptable to gas exchange with the atmosphere, and is constructed of a material which is non-toxic to cells. A variety of vessels suitable for this purpose are well-known in the art, including stirring flasks (Corning, Inc., Corning, N.Y.), stirred tank reactors (Verax, Lebanon, N.H.), airlift reactors, suspension cell retention reactors, cell adsorption reactors, and cell entrapment reactors, petri dishes, multiwell plates, flasks, bags and hollow fiber devices. If agitation is desired, it can be attained by any of a variety of means, including stirring, shaking, airlift, or end-over-end rotation. In addition to maintaining the culture in suspension by agitating the medium (as by stirring or airlift), the culture can also be maintained in suspension by matching the density of the culture medium to the density of the cells or microcarrier beads.

As described in more detail below, in one embodiment of this invention, the culture means and the cell separation means are integrated into a single device. In such a device, the column assembly of the cell separator is modified so that the target cells, after release from the column, flow into the cell culture means, rather than into a fluid collection bag.

Figures 1A, 1B:
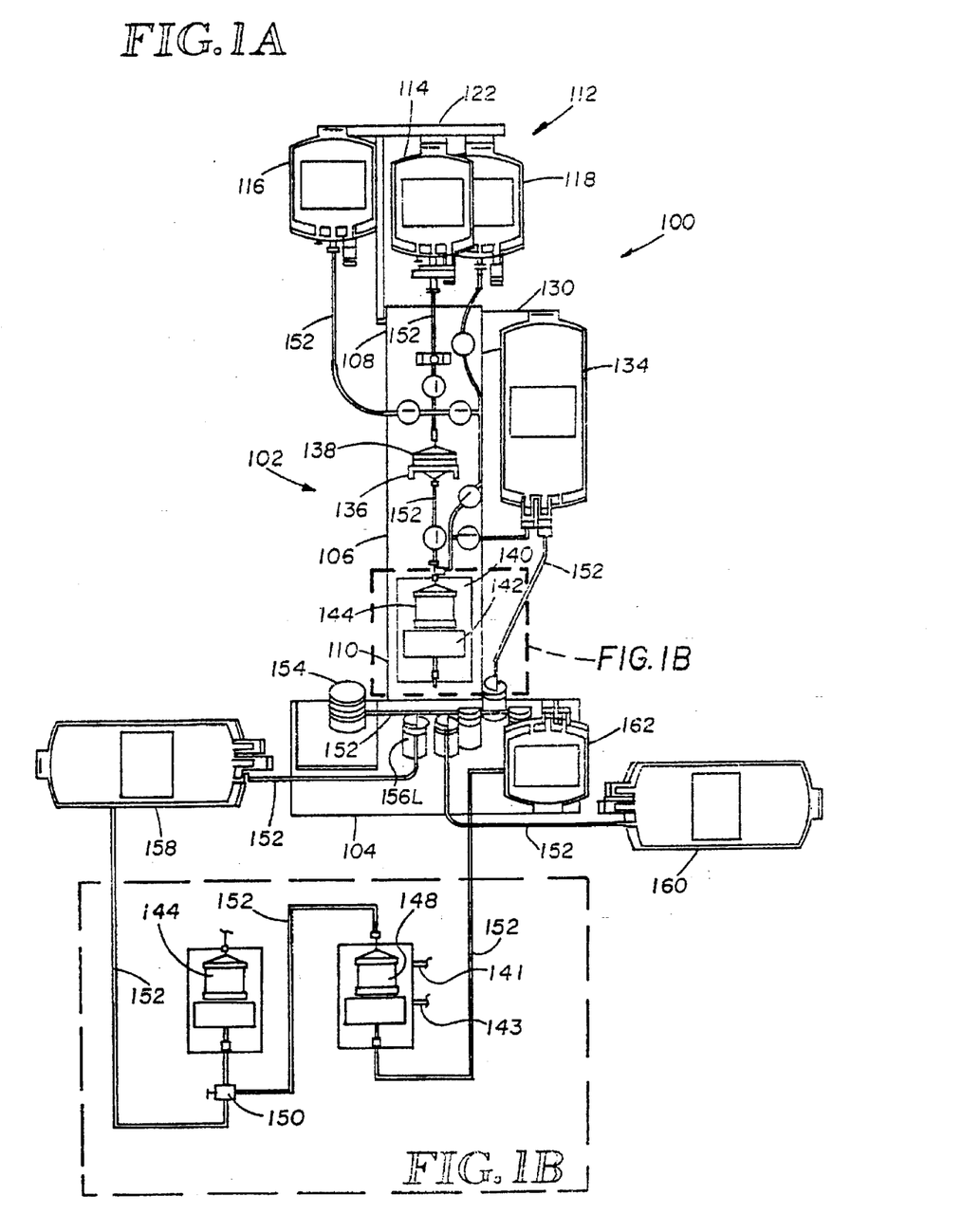
FIG. 1A is an illustrative schematic diagram of a representative device of the present invention.
FIG. 1B is an exploded view of a portion of the column of FIG. 1A, illustrating a culture vessel of the device.

Within this embodiment, an improved cell separator 100, illustrated in FIGS. 1A and 1B, is provided for separating target cells from unwanted cells. The cell separator 100 includes a frame 102 having a base 104 and a support tower 106. The support tower has a top 108 and bottom 110 wherein the bottom 110 is fixed to the base 104. The base 104 is constructed for resting on a substantially horizontal surface such that the support tower 106 extends upright from the base 104. In this construction, the base 104 provides a substantially stable foundation for supporting the support tower 106.

The cell separator 100 also includes a bag holder 112 for receiving a sample fluid supply bag 114, and first and second fluid supply bags 116 and 118, respectively. The sample fluid supply bag 114 is provided for supplying the sample fluid to the cell separator 100. Similarly, the first and second fluid supply bags 116 and 118 are provided for respectively supplying a wash solution and a protein solution to the cell separator 100, each solution for preparing the cell separator for the fluid separation, as will be discussed in more detail below.

The bag holder 112 includes a support rod that is pivotally mounted to the top 108 of the support tower 106 for movement between an upright position wherein the support rod is substantially aligned with the support tower, to a pivoted position, wherein the support rod is angled with respect to the support tower. The support rod is constructed for pivotal movement with respect to the support tower to enable the sample fluid supply bag 114 and the first and second fluid supply bags 116 and 118 to be easily mounted to the bag holder 112 by a user. In the pivoted position, the fluid bags 114–118 may be both mounted and spiked by a user at substantially eye level. Thereafter, the bag holder 112 is pivoted to the upright position to both move the fluid bags 114–118 out of the user's way, and to enable the user to manipulate other portions of the cell separator 100 at substantially eye level.

In a presently preferred embodiment of the invention, movement of the bag holder 112 with respect to the frame 102 is accomplished by pivoting the bag holder 112 with respect to the top 108 of the support tower 106, as described above. However, other means could be provided for moving the bag holder 112 with respect to the frame 102. As an example, the support tower 106 may be constructed to pivot about first and second pivot points, thereby enabling the bag holder 112 to be lowered with respect to the base 104. As another example, the bag holder 112 may be slideably mounted upon the support tower 106, thereby enabling the bag holder 112 to be moveable with respect to the frame 102.

The bag holder 112 further includes a support beam 122 fixed to the support rod 120 and positioned substantially transverse to the support tower 106. The support beam 122 includes a plurality of hooks for receiving the fluid supply bags 114–118.

A fixed bag holder 130 is fixedly mounted to the top 108 of the support tower 106. The fixed bag holder 130 includes a protruding hook for receiving a wash fluid source bag 134. The wash fluid source bag 134 is provided for supplying wash solution to the cell separator for cleansing the cell separator during a separation process.

A pre-column holder 136 is fixed to the support tower 106 intermediate the top 108 and bottom 110 thereof. The pre-column holder 136 is provided for receiving a pre-column 138. The pre-column 138 is provided for pre-filtering the sample fluid prior to the fluid separation to remove large particles and debris from the sample fluid. The pre-column may comprise any of a variety of commercially available devices for pre-filtering the sample fluid. It will be apparent to those skilled in the art, however, that although the present invention is being described as including a pre-column 138, the pre-column 138 and pre-column holder 136 may be omitted from the cell separator 100 without departing from the invention.

One aspect of the subject invention comprises a stirplate assembly 140 that is fixed to the support tower 106 intermediate the pre-column holder 136 and the bottom 110. The stirplate assembly 140 includes a column holder 142 for receiving a column 144. Generally, the column 144 is provided for separating the target particle from the sample fluid. As will be discussed in more detail below, a presently preferred embodiment of the invention employs a column 144 that includes coated beads for positively selecting target cells from the sample fluid. As the sample fluid passes through the column 144, the target cells are retained within the column 144. Advantageously, the stirplate assembly 140 cooperates with the column 144 to provide controlled agitation to the contents of the column 144. Accordingly, after a sufficient quantity of the target cells have been retained within the column 144, the target cell-ligand bond may be broken by controllably agitating the contents of the column 144. Thereafter, the target cells may be eluted from the column 144 and collected as the product of the separation.

The cell separator 100 further includes a sample sensor and a column sensor for sensing changes in optical density of fluid flowing in a tubing 152. The sample sensor is fixed to the top 108 of the support tower 106 for sensing changes in optical density of fluid flowing from the sample fluid supply bag 114. The column sensor 150 is fixed to the base 104 of the frame 102 for sensing changes in optical density of fluid flowing from the column 144. Each of the sample sensor and column sensor comprises an optical sensor.

The sample sensor is constructed for providing a sample sensor signal to indicate the change in optical density of the fluid coming out of the sample fluid supply bag 114. The column sensor is constructed for providing a column sensor signal to indicate the change in optical density of the fluid flowing from the column 144. Both the sample sensor signal and the column sensor signal are provided to a data processor assembly for use in controlling the operation of the cell separator 100.

The cell separator 100 further includes a peristaltic pump 154 for pumping fluid between the plurality of fluid bags 114–118 and 134 and the fluid tubing 152. The peristaltic pump is responsive to a pump control signal provided by a data processor assembly for controlling the speed and direction of flow of fluid in the fluid tubing 152. The peristaltic pump 154 is further constructed for providing a pump speed signal to the data processor. The pump speed signal is indicative of the speed and direction that fluid is being pumped through the fluid tubing. An appropriate peristaltic pump for performing the above-described operation may be readily constructed by one skilled in the art. In a presently preferred embodiment of the invention, the peristaltic pump comprises a Cavro 4708-5 peristaltic pump as provided by Cavro Scientific Instruments, Inc. (Sunnyvale, Calif.). It will be apparent, however, that other apparatus for providing the functions of the peristaltic pump may readily be substituted for the Cavro pump.

The cell separator 100 includes a plurality of valves for controlling the path that the fluid flows through the fluid tubing 152. Each of the valves includes a solenoid (not shown) and plunger separated by a valve channel sized to receive the fluid tubing 152. Each valve is responsive to a respective valve control signal for displacing the plunger to collapse the fluid tubing and thereby prevent the flow of fluid through the valve. The plurality of valves 156 are positioned to receive respective portions of the fluid tubing 152, thereby to define a plurality of fluid flow paths between the fluid bags. The data processor assembly is constructed to provide the plurality of valve control signals for controlling the path that the fluid flows through the fluid tubing 152. In a presently preferred embodiment of the invention, the data processor assembly comprises a personal computer as is commercially available.

The cell separator 100 permits substantially hands-free operation by a relatively unskilled operator. Ideally, the fluid bags 114-118 and 134, along with the tubing 152 and column 144, are provided as disposable apparatus constructed for use during only a single separation process.

In operation, the user of the cell separator 100 pivots the bag holder 112 to mount the fluid bags thereon and to spike the fluid bag for operation. The bag holder 112 is then returned to the upright position and the tubing properly placed within the sensors and the valves. Once the cell separator 100 is thus configured for operation, the user need only monitor the operation for abnormal circumstances that cannot be controlled by the data processor assembly.

After the user initiates the cell separation process, the data processor assembly selectively opens and closes the valves to permit wash fluid to flow from the wash fluid bag 134 sequentially through the valves. This fluid flow acts to remove air from the tubing 152 and column 144 and to cleanse the tubing of impurities that may be in the tubing from its manufacture.

After the initial cleansing, the data processor assembly controls the valves to prime the tubing by allowing fluid to flow from the second fluid supply bag 118 through the valves to the pre-column 138, the column 144, and into a waste bag 158. The flow of fluid in this manner primes the column and tubing with a protein solution selected to prevent substantial bonding of the target cells to the tubing. Subsequently, the microprocessor controls the valves to permit fluid to flow from the first fluid supply bag 116 through the valves into the pre-column 138, the column 144, and into the waste bag 158. Simultaneously, fluid is permitted to flow from the wash fluid source bag 134 into the column 144, and the valve 156L and into the waste bag 158. This fluid flow permits rinsing of the tubing and column to remove excess protein and to further wash residual material that may be remaining in the tubing and column from manufacture.

After the cell separator 100 has primed the tubing, it runs the cell separation process. Initially, the data processor assembly opens the valves to wet the tubing and filter, coupling the sample bag 114 to the tubing 152. Thereafter, the valves are controlled with the peristaltic pump to permit slow loading of the sample via the column. During this phase, the sample fluid is slowly permitted to pass through the column so that the target cells may bind with the substrate of the column 144. The unwanted material of the sample fluid is discarded in the waste bag 158. During the loading process, the data processor assembly monitors the sample sensor signal and the column sensor signal to determine whether all of the sample fluid has been provided and to determine whether a significant amount of target cells are being discarded in the waste bag 158. If either of these events occur, the data processor assembly will discontinue the loading step and move to another portion of the cell separation.

As noted above, the data processor assembly monitors the sample sensor signal provided by the sample sensor to determine when the sample fluid supply is empty. Those skilled in the art will appreciate that the optical density of the fluid flowing past the sample sensor will change dramatically at the instant the last portion of the sample fluid passes by the sample sensor. At that point, the microprocessor assembly determines that no further sample fluid is available, and that the column should be emptied.

After all of the sample fluid has been passed through the column 144, the microprocessor assembly will wash the column to remove non-specifically bound portions of the sample fluid. The valves will be controlled to permit fluid to flow from the wash fluid source bag 134 to the waste bag 158. During this main column wash step, the microprocessor assembly may be controlled to provide very light agitation to the column by providing a drive signal to a stirplate assembly to slowly rotate a stirbar within the column 144. However, in a presently preferred embodiment of the invention, no agitation is provided during the column wash step.

After the column wash step, the target cells are eluted from the column. During this step, the microprocessor assembly controls the valves to permit fluid to flow from the column 144 to a culture vessel 148. The culture vessel 148 contains culture medium comprising nutritive medium and a source of growth factors. The configuration of the culture vessel is described above. As shown in FIGS. 1A and 1B, a culture means is provided comprised of the culture vessel 148, an agitation means for agitating the contents of the vessel to a degree sufficient to substantially maintain the cells in suspension, a temperature control means, and perfusion means through port 143 by which gas tension and humidity can be controlled and medium can be added or removed. In addition, the culture vessel 148 is provided with a port 141 for the purpose of sampling. Subsequent to the step of culturing, the precursor cells flow through the tubing 152 to the cell collection bag 162.

Microcarrier Beads

If desired, separated precursor cells can be inoculated into culture medium containing microcarrier beads, to which at least a fraction of the cells are capable of attaching. Generally, such beads consist of a polysaccharide gel (such as agarose or carageenan) or a fibrous polymer (such as collagen). The density of the beads can be varied, for example, by weighting them with an inert material (such as silica) or lightening them by entrapping a gas within. A preferred bead is sold by Pharmacia (Piscataway, N.J.) as CYTODEX™ 3 microcarrier beads.

Incubation Conditions

Generally, separated precursor cells are incubated in a humidified atmosphere consisting of 5–10% carbon dioxide and 3–20% oxygen at a temperature of about 37° C. The desired humidity, oxygen and carbon dioxide tensions, and temperatures are usually maintained by culturing the cells in an incubator. However, it is possible to maintain the desired conditions by perfusing the vessel(s) in which the cells are growing with pre-warmed medium, the carbon dioxide and oxygen content of which has been or is continuously adjusted during perfusion.

The length of the incubation period is determined by the degree of expansion in cell number which is desired. Generally, cells are cultured for 4–21 days, more often for 4–14 days. Culture for 4–14 days generally results in a 5-fold or greater expansion in the number of cells (relative to the starting inoculum) and approximately a 7-fold or greater expansion in the number of CFU-GM (see below).

Cell Density

Cultures of separated precursor cells may be seeded at densities between about $1 \times 10^3$ cells/ml and $4 \times 10^6$ cells/ml. Most preferred densities are between about $1 \times 10^3$ cells/ml and $1 \times 10^4$ cells/ml.

Cell Expansion

Precursor cells are referred to as having increased or expanded in number if their number after a defined period of incubation is greater than the number of cells with which the culture was inoculated. Of particular interest in the context of the present invention is the increase in number of hematopoietic precursor cells. This may be determined by any of a variety of assays, including determination of the number of CD34-positive cells (e.g., by immunofluorescence microscopy or flow microfluorimetry) and/or determination of the number of CFU-GM. Because each of these assays measures different properties, the magnitude of the increase as determined by two or more different methods may be different. It may also be informative to determine the total number of cells (of all types) in the culture. This may be performed simply by counting the cells, using a hemacytometer or a Coulter counter.

To determine the number of CFU-GM at any given time point, cells are inoculated into Iscove's methylcellulose medium (Terry Fox Laboratories, Vancouver, BC) at approximately $10^3$ cells/ml. The medium contains approximately 0.8% methylcellulose, 30% fetal calf serum, 1% BSA, $10^{-4}$M 2-mercaptoethanol, 3 units/ml EPO, and 5% (by volume) PHA-stimulated-lymphocyte-conditioned medium. Aliquots of the medium containing cells are plated in triplicate in 35 mm tissue culture dishes and incubated for approximately 14 days at 37° C. in a humidified atmosphere containing 5% carbon dioxide. At the end of this time, the number of colonies containing more than 50 cells of myeloid (CFU-GM) or erythroid (BFU-E) origin is scored using an inverted microscope.

To determine the number of CD34-positive cells by flow microfluorimetry, approximately $0.1–1.0 \times 10^6$ cells are suspended in 100 ul of an appropriately diluted monoclonal anti-CD34 antibody, such as Q-Bend 10 (Biosystems Ltd., Waterbeach, Cambridge, England) at 5 ug/ml. Cells and antibody are incubated for 15–30 minutes at between 0° and 4° C., washed two times in phosphate-buffered saline (PBS) containing 1% (w/v) BSA to remove unbound antibody. Bound antibody is then visualized by the addition of 100 ul of a 1:100 dilution of goat anti-mouse IgG conjugated with phycoerythrin (PE). The mixture is incubated for 15–30 minutes at 0°–4° C., then the cells are washed as above, stained with 200 ul of propidium iodide (1 ug/ml), and analyzed on a fluorescence-activated cell sorter. As a control for non-specific staining by the PE conjugate, cells are labeled with an isotype-matched mouse IgG1 antibody which does not react with CD34 cells.

Cell Harvesting

When the desired degree of cell expansion has taken place, cells are harvested from the culture vessel(s), for example, by centrifugation or filtration. Generally, the cells are washed one to three times with fresh medium or buffer. At this stage, they may be resuspended to a desired concentration in a physiological solution (i.e., suitable for infusion into patients). The resultant cell suspension may be infused in a single bolus or over a period of hours, depending on the volume to be given. Other substances may also be added to the cell suspension, for example, growth factors such as G-CSF, before it is given to the patient.

Alternatively, after harvesting the cells from culture and before infusing them into the patient, it may be desirable to re-separate the cells into CD34-positive and -negative fractions. This can be accomplished, as described above, by positive selection of CD34-positive cells, by negative selection of CD34-positive cells, or by a combination of the two. It is preferred to separate the harvested cells into CD34-positive and -negative fractions by immunoaffinity chromatography, using a biotinylated anti-CD34 monoclonal antibody and immobilized avidin, as described above.

If the cells are not going to be used immediately, it may be desirable to freeze them. A particularly preferred method of freezing hematopoietic stem cells is described in co-pending patent application U.S. Ser. No. 07/780,487, filed Oct. 23, 1991. Briefly, CD34-positive cells are suspended in a physiologically acceptable medium containing human autologous plasma and DMSO and frozen at a controlled rate.

The following examples are offered by way of illustration, and not by way of limitation.

EXAMPLES

EXAMPLE 1

A buffy coat was prepared from human cadaveric bone marrow and separated into CD34-positive and CD34-negative cells by immunoselection, using the CEPRATE SC Stem Cell Concentrator, available from CellPro, Inc. (Bothell, Wash.), according to the manufacturer's directions. The resultant CD34-positive cell fraction contained approximately 70% CD34-positive cells, as determined by flow microfluorimetry using the anti-CD34 monoclonal antibody Q-Bend 10 and a phycoerythrin-conjugated goat anti-mouse Ig second step.

$1 \times 10^5$ CD34-positive cells/ml were inoculated into 150 ml of X-VIVO-10 medium (BioWhittaker, Walkersville, Md.), containing 5% human plasma, 50 ng/ml SCF (R&D Systems, Minneapolis, Minn.), 10 ng/ml Il-3 (R&D Systems), 0.5 ng/ml Il-1 alpha (R&D Systems), and 50 ng/ml Il-6 (R&D Systems), in a 150 ml stirring flask (#26501-125, Corning, Inc., Corning, N.Y.). The culture was stirred at 40 rpm in a 37 degrees C., humidified atmosphere containing 5% carbon dioxide. For comparison, CD34-positive cells were cultured under identical conditions, but without stirring.

The total number of cells in each culture vessel (stirred and unstirred) was determined after 7 and 14 days incubation. The number of CFU-GM on day 7 was also determined for each culture. The data are shown in the Table 1 below.

TABLE 1

| Type of Culture | Fold-Increase in Number of Cells Day 7 | Fold-Increase in Number of Cells Day 14 | Fold-Increase in Number of CFU-GM Day 7 |
|---|---|---|---|
| stirred | 7.6 | 14.3 | 6.9 |
| unstirred | 7.7 | 7.8 | 3.6 |

As can be seen from the table, the stirred culture contained approximately twice as many cells as the unstirred culture on day 14. More importantly, the stirred culture contained twice as many hematopoietic precursor cells, as judged by the number of CFU-GM, on day 7 as the unstirred culture.

The percentage of cells which were CD34-positive was also determined by flow microfluorimetry for each culture after 7 and 14 days. The stirred culture contained 5.7% CD34-positive cells on day 7 and 1.2% CD34-positive cells on day 14. By contrast, the unstirred culture contained only 2.9% CD34-positive cells on day 7 and 1.5% CD34-positive cells on day 14.

EXAMPLE 2

Preparation of an Avidinated Biogel

A. CARBOXYLATION OF A POLYACRYLAMIDE GEL

Seventeen grams of dry Biogel P-60™ (50–100 mesh (wet), coarse beads) (BIORAD, Catalog No. 150, 1630, Richmond, Calif.) are added to 1.5 l of 0.5M $NaHCO_3$/0.5M $Na_2CO_3$. The pH is adjusted to 10.5 with NaOH and carefully stirred with a mixer (RZR1, Carfamo, Wiarton, Ontario, Canada) so as not to damage the beads for approximately 20 to 30 minutes. The mixture is then placed in a 60° C. water bath. After the mixture reaches a temperature of 60° C., it is incubated for an additional 2 hours (at 60° C.) with occasional stirring. The mixture is then removed from the water bath, and placed in an ice bath to bring the mixture temperature down to room temperature.

The beads are washed several times with distilled or deionized water, followed by several washings with PBS using a coarse glass filter connected to a vacuum. The carboxylated gel may be stored in PBS at 4° C., and is stable for up to one year if sterilized or stored with a preservative.

B. AVIDIN CONJUGATION OF CARBOXYLATED BIOGEL

PBS is first removed from a measured amount of carboxylated Biogel by filtering with a coarse glass filter connected to a vacuum. The gel is then equilibrated in distilled or deionized water for 15 to 30 minutes. Equilibration in water causes an expansion of the gel to a volume of about 4 times its previously measured amount. The gel is resuspended in 10 ml of distilled or deionized water for each ml of gel (as originally measured in PBS).

Thirty mg of 1-ethyl-3-(3-dimethylaminopropyl) carbodiimide (EDC-HCl) (Sigma Chemical Co., Catalog No. E7750, St. Louis, Mo.) is added for each ml of gel as originally measured. The pH is rapidly adjusted to 5.5 by dropwise addition of HCl. Care is taken to maintain the pH at 5.5; pHs of less than 5.0 or greater than 6.0 result in significantly less activation of the Biogel. The mixture is stirred for five minutes.

Avidin (International Enzymes, Inc., Fallbrook, Calif.) is dissolved at a concentration of between 10 and 100 mg/ml in deionized water. Next, 1 mg of avidin is rapidly added for each ml of gel (as originally measured in PBS). The mixture is stirred for 1.5 hours. Next, 2M glycine is added to give a final concentration of 0.2M glycine in the mixture, and stirred for an additional 1 hour.

The gel is washed with several volumes of PBS using a coarse glass filter and vacuum, and stored in PBS at 4° C. The gel is stable for approximately one year.

EXAMPLE 3

Isolation of Engrafting Cells

A. PREPARING THE BUFFY COAT CELLS

A sample of bone marrow is centrifuged at 240×g for 15 minutes. The plasma is removed (and is retained for later use), and the remaining buffy coat cells are centrifuged once more at 240×g for 15 minutes in order to remove red blood cells. The buffy coat cells are washed twice with RPMI by centrifugation at 180×g for 10 minutes. The cells are then resuspended to a final concentration of $1 \times 10^8$ white cells/ml in RPMI plus 1% BSA.

B. INCUBATION OF BUFFY COAT CELLS WITH ANTIBODY

The suspension of buffy coat cells is incubated with a final concentration of 20 µg/ml biotinylated anti-CD 34 antibody (CellPro®, Bothell, Wash.) at room temperature for 25 minutes. The antibody-cell mixture is then washed twice with PBS by centrifugation at 180×g for 10 minutes. The cells are then resuspended at a concentration of $1 \times 10^8$ white cells/ml in PBS.

C. COLUMN OPERATION AND RESULTS

A CEPRATE LC™ (CellPro®, Bothell, Wash.) separating system was utilized essentially according to the manufacturer's instructions. Briefly, the instrument was set up, the tubing connected, reagent's were loaded, and the process run was begun with the antibody treated cells. The cells were pumped through the column, the column was washed with PBS, then the adsorbed cells were released via the magnetically driven impeller. The adsorbed cells were accumulated in a collection bag.

D. RESULTS

Ten billion bone marrow cells were passed through the column; 200 million of the cells were bound to the column and were recovered in the collection bag. Viability of the collected cells was 91% as measured by trypan blue exclusion. The collected cells were 75% CD $34^+$ as measured by FACS analysis.

EXAMPLE 4

Determination of CFC Viability and Recovery

One ml per 35 mm plate of Iscove's Methylcellulose (Terry Fox Laboratories, Vancouver, British Columbia, Canada) supplemented with 2 mM L-glutamine and 50 ng/ml gentamicin was warmed to 37° C. Cells were plated in triplicate at 3-fold dilutions to improve the accuracy of the assay. The highest number of cells plated was $10^5$/plate except for column-purified cells which were plated at $3 \times 10^3$ and less. The cells were spread evenly over the surface of each plate and then incubated in a humidified incubator at 37° C. with 5% $CO_2$ in air for 10 to 14 days. Colonies were counted if they contained more than 50 cells and scored as CFU-GM, BFU-E, or other (e.g., CFU-GEMM). The number of various types of colonies were summed to give the total number of colony-forming cells (CFCs).

EXAMPLE 5

Stem Cell Expansion

A. COMPARISON OF THE EXPANSION OF SEPARATED STEM CELLS VERSUS STEM CELLS IN WHOLE MARROW

Stem Cells which were purified as described above in Example 3 were grown in a solution containing RPMI 1640, 10% Fetal Bovine Serum HYCLONE®, Logan, Utah), 50 ng/ml Stem Cell Growth Factor, 50 ng/ml Interleukin-3, 20 ng/ml Granulocyte-Macrophage Colony-Stimulating Factor, and 20 ng/ml Granulocyte Colony-Stimulating Factor. The cells were plated at $10^6$ per plate in 1 ml of media. On days 7, 14, and 21 cells were removed and replated for CFC assays as described in Example 4. Viable cells were counted by hemacytometer using trypan blue. Stem cell separation prior to culturing the cells dramatically improved stem cell growth and expansion.

B. FACTORS WHICH CAUSE STEM CELL EXPANSION

In order to determine what growth factors are useful for expanding stem cells, the following assay was undertaken. Briefly, stem cells which were purified as described above, were plated at a density of $10^6$ cells per plate in Corning 35 mm plates. The cells were fed a solution containing RPMI 1640 supplemented with 10% fetal bovine serum, and various combinations of the following growth factors: (1) 50 ng/ml Stem Cell Growth Factor (Amgen, Thousand Oaks, Calif.), (2) 50 ng/ml Interleukin-3, (3) 20 ng/ml Granulocyte-Macrophage Colony-Stimulating Factor (Immunex, Seattle, Wash.), and (4) Granulocyte Colony-Stimulating Factor (Genzyme, Cambridge, Mass.). Media containing SCF expanded stem cells (as determined by the increase in CFC number).

EXAMPLE 6

Growth of Separated CD34-Positive Cells on Microcarrier Beads

Five grams of CYTODEX 3 Microcarrier Beads (Pharmacia, Piscataway, N.J.) were resuspended in 500 ml of $Ca^{++}$, $Mg^{++}$-free PBS. The beads were allowed to settle out of solution, the PBS was decanted, and the beads were resuspended in an additional 500 ml of PBS. This sequence was repeated a total of two times. After the final wash, the beads were autoclaved in a glass bottle on the fluid cycle setting of an autoclave. The beads were allowed to cool, were washed once in Iscove's modified Dulbecco's medium (IMDM) and stored at room temperature in 50 ml of minimal essential medium (MEM).

A buffy coat was prepared from human cadaveric bone marrow and separated into CD34-positive and CD34-negative cells by immunoselection, using the CEPRATE SC stem cell concentrator (CellPro, Inc., Bothell, Wash.), according to the manufacturer's directions. CD34-positive cells were frozen at a density of $20\times10^6$ cells/ml in TC-199 medium (Sigma, St. Louis, Mo.) containing 7.5% DMSO (Tera Pharmaceutics, Inc., Buena Park, Calif.), 20% human plasma, and 10 units/ml of heparin (Sigma), using a controlled rate freezer (CRYOMED, Forma Scientific, Harietta, Ohio). After freezing, cells were transferred to liquid nitrogen for storage.

Frozen CD34-positive cells were thawed in a 37° C. waterbath and gradually diluted with ten volumes of X-VIVO-10 medium containing 10 units/ml heparin and 100 units/ml DNase (Sigma). The cells were washed once by centrifugation. Cells were plated in a 100 mm×15 mm split compartment petri dish (Falcon, #1003) at a concentration of $10^5$ cells/ml (5 ml to a side) in X-VIVO-10 medium, containing 5% human plasma, 2.5 ng/ml IL-1, 50 ng/ml IL-6, 10 ng/ml IL-3, and 50 ng/ml SCF (all from R&D Systems, Minneapolis, Minn.). One hundred ul of CYTODEX beads, prepared as described above, were added to one side of the dish, but not the other. The dish was incubated at 37° C. in a humidified atmosphere containing 5% carbon dioxide.

The total number of cells, the percentage of cells which were CD34-positive, the viability, and the number of CFC/$10^5$ cells were determined on each side of the dish after 7 days' culture. There was an approximately 11-fold expansion in cell number in the control (no beads) versus a 4-fold expansion in the presence of beads. The latter number, however, is believed to be an underestimate of the degree of expansion, as many of the cells remained adhered to or entrapped within the beads. The percentage of CD34-positive cells in the control was approximately 0.93% versus 0.76% for the cells grown on beads. The number of CFC/$10^5$ cells were approximately equal between the two groups, at 2700 for the control and 2567 for the beads. Viability was 83% in the control and 91% for the beads.

EXAMPLE 7

Expansion of Hematopoietic Precursor Cells

Comparison of Separated CD34-Positive Cells with Whole Marrow

Separated CD34-positive cells were prepared as described in Example 6 above and cultured at varying densities in X-VIVO-10 medium containing 10% allogeneic human plasma or 10% fetal calf serum (FCS). Cells were inoculated into 35 mm culture dishes (Corning Glass Works, Corning, N.Y.), 24-well Linbro multiwell plates (Flow Laboratories, McLean, Va.) or 25 $cm^2$ flasks (Corning), and incubated for 7 days at 37° C. without medium exchange.

Figure 2:
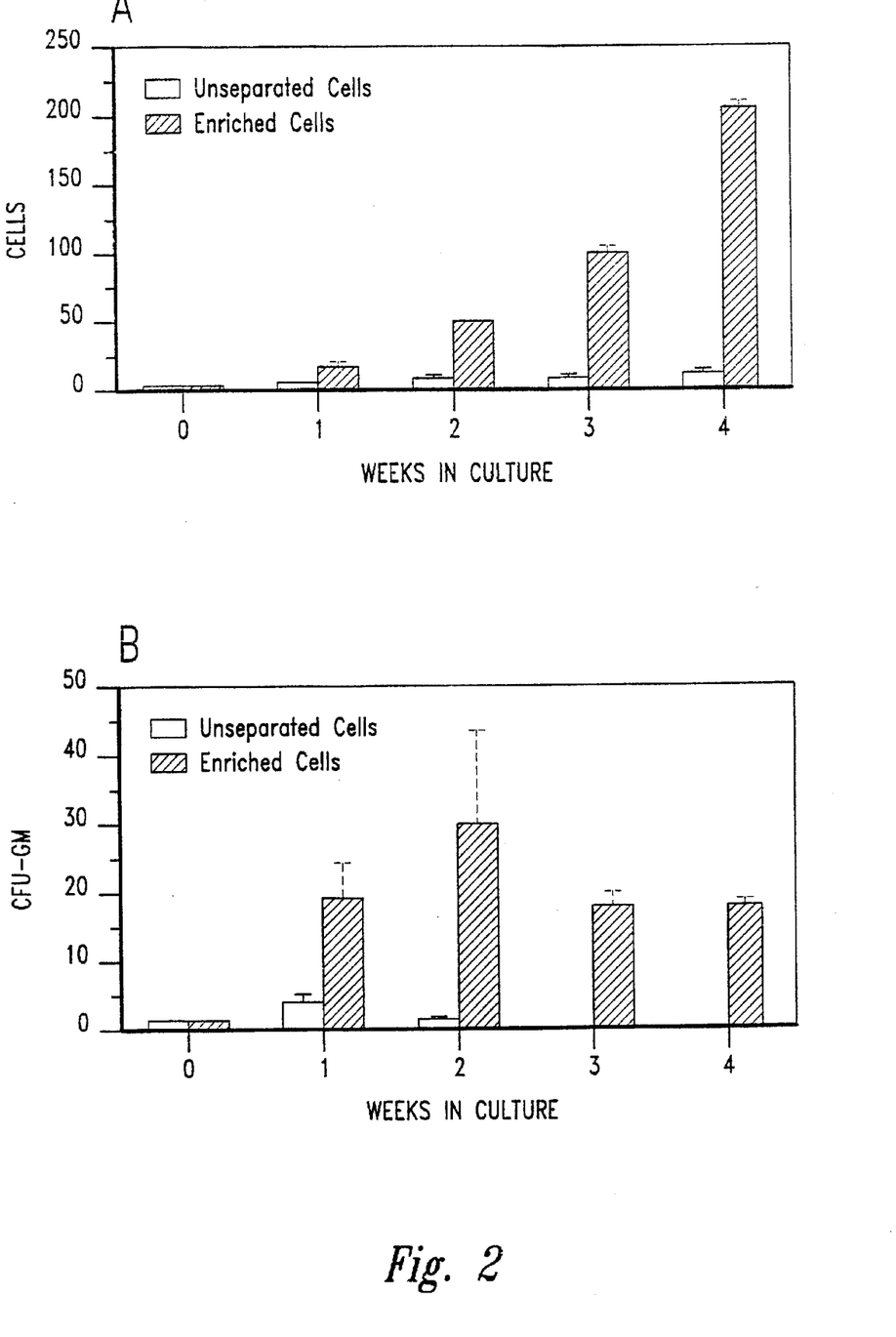
FIG. 2 is a pair of graphs depicting the expansion of cells and CFU-GM numbers using unseparated bone marrow (unseparated cells) or CD34$^+$ marrow cells (enriched cells) in a long-term suspension flask culture system with SCF (50 ng/ml)+IL-3 (50 ng/ml)+GM-CSF (20 ng/ml). Cells were cultured in flasks for up to seven weeks. Data are the mean ±1 SEM from two experiments. Block A: *Fold increase in cell numbers. Block B: *Fold increase in CFU-GM numbers. The expansion value in the Y-axis represents fold increase over the start number. The formula is as follows: starting value: 100%=1.0. Expansion=Total number at end of culture×100%/Total number at start of culture.

As illustrated in FIG. 2, the total cell count and the number of CFU-GM were increased by separation of CD34-positive cells prior to culture. Cultures initiated with unseparated (whole) bone marrow generated decreasing numbers of cells over time and by week 3 of culture had lost all CFU-GM activity. By contrast, cultures initiated with separated CD34-positive cells showed a 15–100-fold expansion in total cell number and an 18–30-fold expansion in CFU-GM, relative to the starting inoculum, and continued to generate cells and CFU-GM for up to seven weeks in culture.

Figure 3:
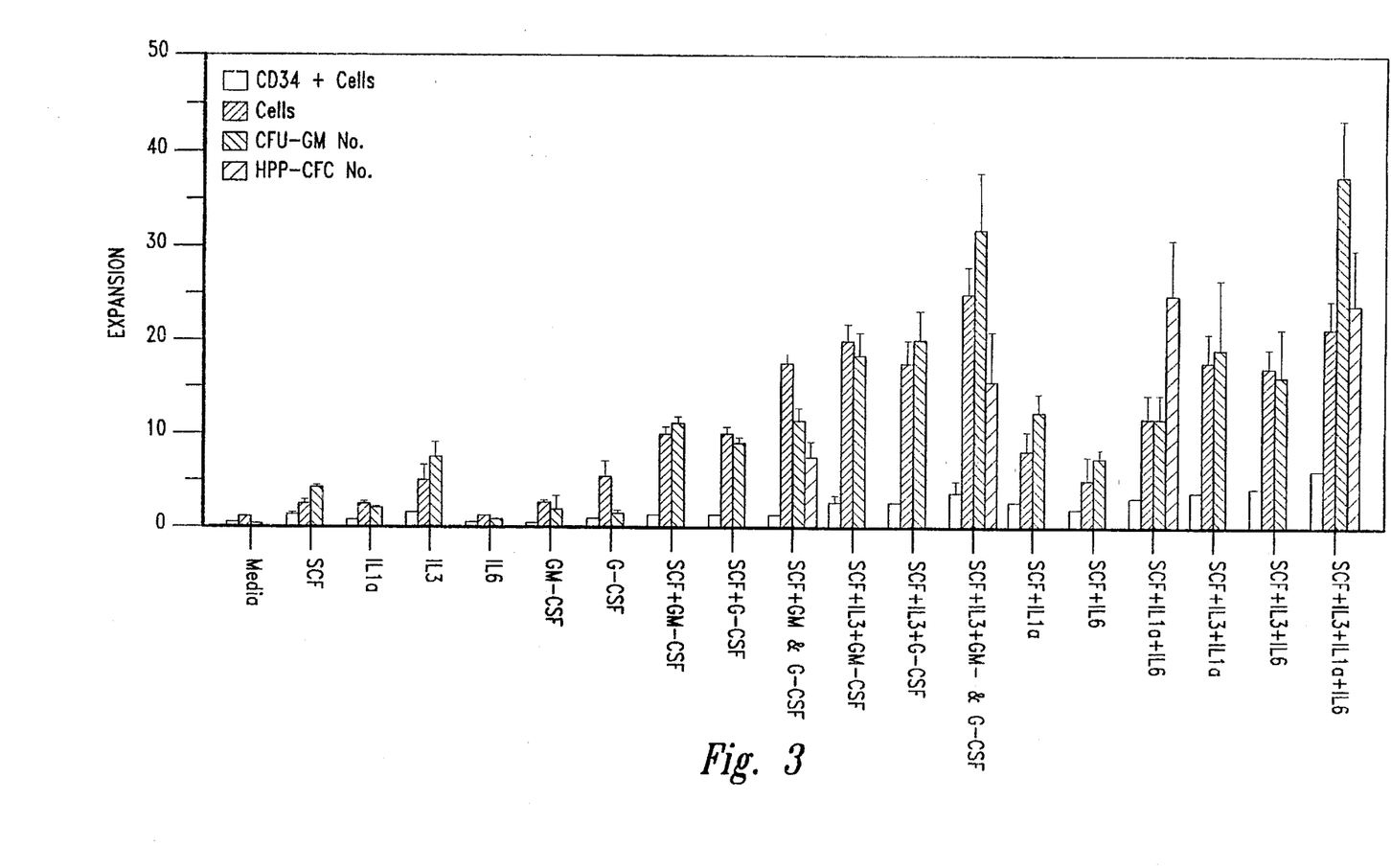
FIG. 3 is a graph depicting the effect of different cytokines alone or in combinations, on expansion of CD34$^+$ cells, CFU-GM, HPP-CFC and cell numbers. CD34$^+$ enriched marrow cells were cultured at a concentration of $1-4 \times 10^5$/ml in suspension culture with 10% human plasma and SCF (50 ng/ml), IL-3 (500 ng/ml), IL-1α (0.5 ng/ml), IL-6 (50 ng/ml) and GM and G-CSF (20 ng/ml) for seven days. Data are the mean ±1 SEM from three experiments.

As illustrated by FIG. 3, certain combinations of growth factors (cytokines) promote hematopoietic precursor cell expansion more effectively than others. Among single growth factors, IL-3 had the largest effect on CFU-GM numbers (7.6-fold expansion), while G-CSF has the largest effect on total cell number (5-fold expansion). Among combinations, the combination of SCF/IL-3/IL-1 alpha/IL-6 generated the largest increase in CD34-positive cells (6-fold) and CFU-GM numbers (38-fold expansion).

Figure 4:
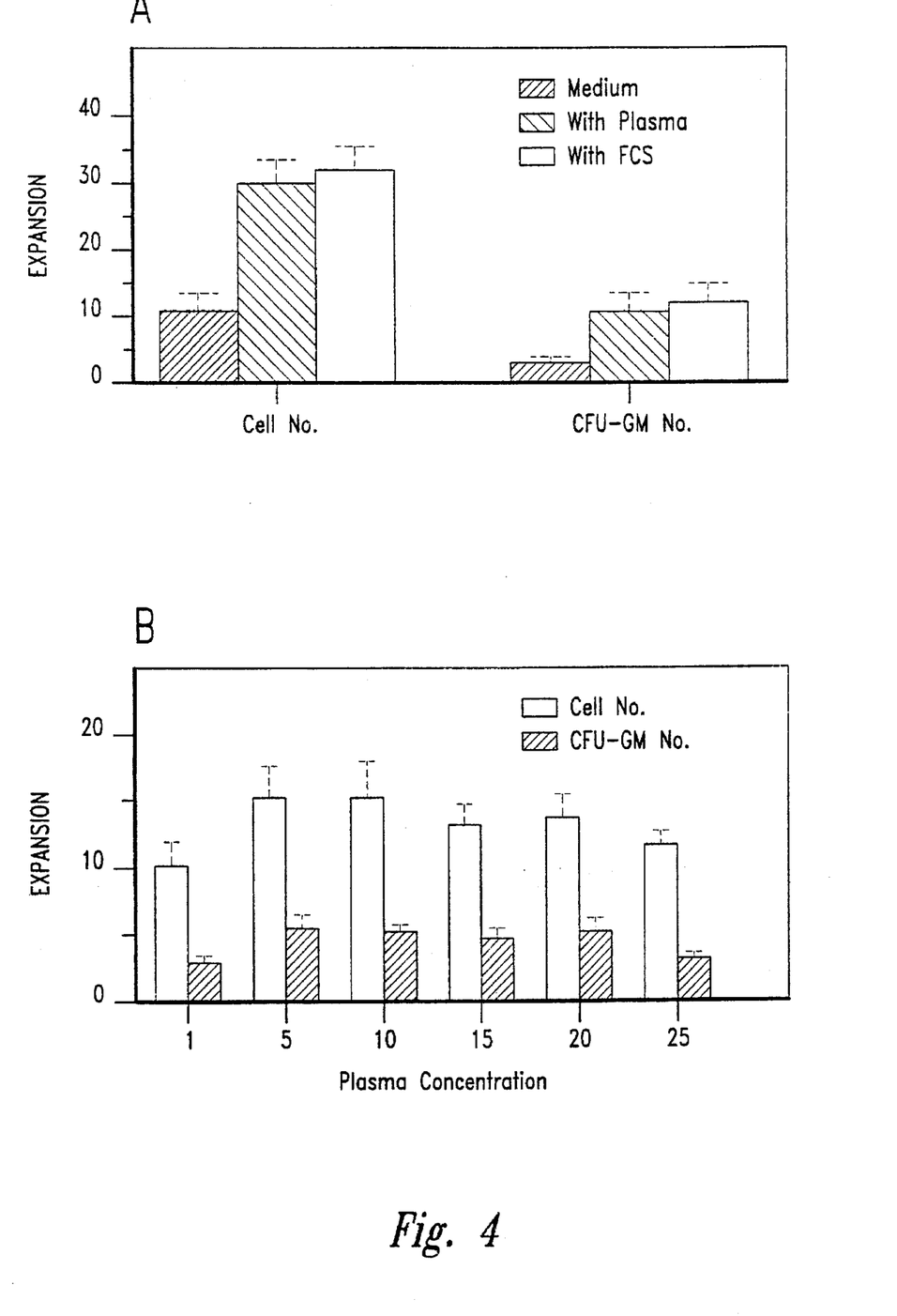
FIG. 4, Block A is a graph depicting the effect of human plasma or FCS on expansion of CFU-GM and cell numbers. CD34$^+$ cells were cultured in X-VIVO-10 serum free medium containing 10% human plasma (with plasma) or 10% FCS (with FCS) or no plasma or no FCS (medium) for seven days in suspension culture using SCF+IL-3+GM-CSF at 50, 50, 20 ng/ml, respectively. Data are the mean ±1 SEM from three experiments. P value between medium and with plasma or FCS group both in expansion of cells and CFU-GM are <0.001.

As illustrated by FIG. 4, Block A, the addition of either 10% human plasma or 10% FCS to the culture medium resulted in a 3-fold greater expansion in total cell number than comparable cultures lacking plasma or serum. Similarly, there was a 4-fold greater expansion in the number of CFU-GM in the presence of plasma or serum relative to its absence. FIG. 4, Block B, shows that the optimal concentration of human plasma for expansion is 5%.

Figure 5:
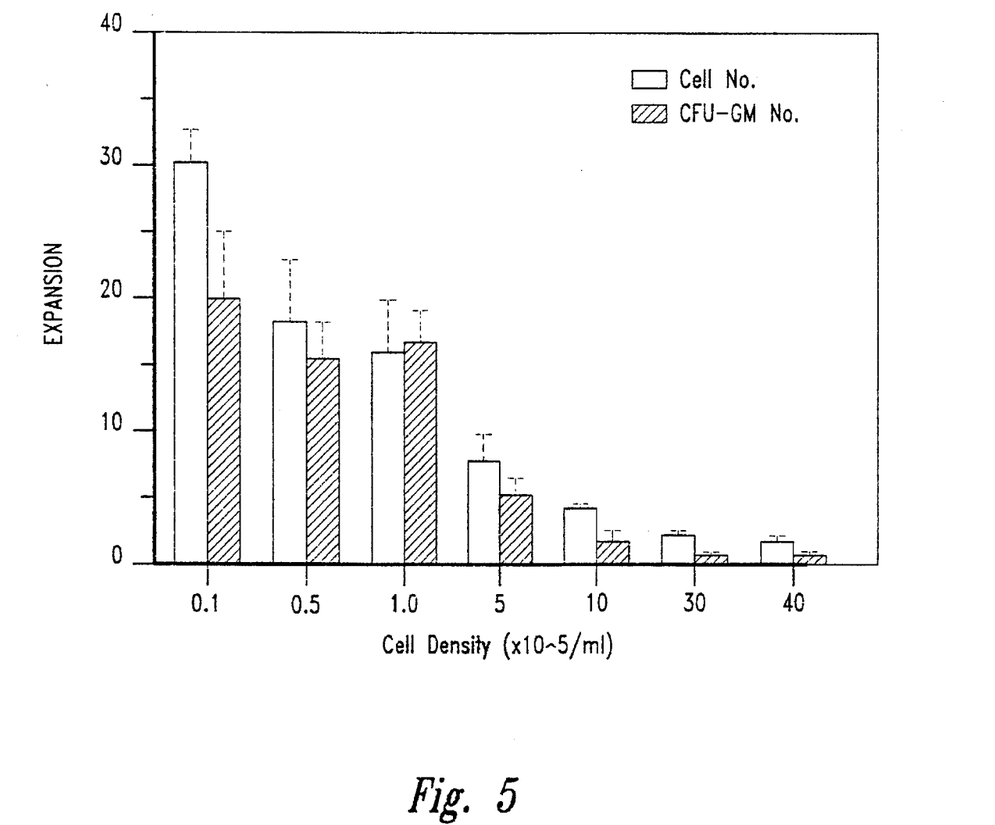
FIG. 5 is a graph depicting the effect of varying cell density on expansion of cell number and CFU-GM numbers. CD34$^+$ enriched cells were cultured for seven days in suspension culture using 10% human plasma and SCF+IL-3+GM-CSF at 50, 50, 20 ng/ml, respectively. Data are the mean ±1 SEM from four experiments. P value between 0.1 and $1.0 \times 10^5$/ml group in cell numbers is <0.05, but in CFU-GM numbers is >0.2. P value between 1.0 and $5 \times 10^5$/ml group in expansion of cells and CFU-GM are <0.05, and also is <0.05 in between 5.0 and $10.0 \times 10^5$/ml group both in expansion of cells and CFU-GM numbers.

As illustrated in FIG. 5, total cell expansion and CFU-GM expansion are both dependent on the starting cell density. An initial cell density of $1\times10^4$ cell/ml or less appears to be optimal.

Table 2 illustrates the effect of oxygen tension on the expansion of hematopoietic precursor cells after 7 days in culture. By all measures (total cell number, CFU-GM, and HPP-CFC), greater expansion is obtained at 5% oxygen than at 20% oxygen (the concentration in ambient air). In addition, it appears generally that an oxygen tension below ambient air is preferred.

TABLE 2

The effect of lower oxygen on the expansion of CFU-GM,
HPP-CFC and total cell numbers.

| | Cell No.* | CFU-GM No.* | HPP-CFC No.* |
|---|---|---|---|
| 5% O2 | 5.5 ± 0.2 | 39.2 ± 0.8 | 33.3 ± 3.8 |
| 20% O2 | 3.6 ± 0.17 | 27.1 ± 0.6 | 7.6 ± 0.9 |
| P value | <0.01 | <0.01 | <0.01 |

CD34+ marrow cells were cultured at a concentration of $3 \times 10^5$/ml in X-VIVO-10 medium containing 10% human plasma and SCF + IL3 + IL1α + IL6 at 50, 5, 0.25 and 50 ng/ml, respectively for seven days. *Fold increase of start number (1.0).

In summary, separated CD34-positive cells can be grown in culture for up to 7 weeks, without an established stromal layer, provided that they have an appropriate source of growth factors. Under these conditions, they continue to generate hematopoietic precursor cells. Furthermore, provided the cells are plated initially at a low density (as described above), cultures can be maintained and will continue to expand without medium exchange, reducing the cost of culture, the labor involved, and the risk of contamination.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for increasing the number of human hematopoietic precursor cells in vitro, comprising:

separating CD34-positive human hematopoietic precursor cells from CD34-negative cells present in a blood product;

inoculating the separated precursor cells at an initial density of between $1\times10^3$ cells/ml and $4\times10^6$ cells/ml into a culture vessel containing a culture medium comprising a nutritive medium and hematopoietic growth factors effective for expansion of CD34-positive cells, with the proviso that said culture medium and culture vessel contain no stromal cells or stromal cell conditioned medium; and culturing the precursor cells under conditions and for a time sufficient to increase the number of precursor cells relative to the number of precursor cells present after separation of hematopoietic cells from said blood product.

2. The method of claim 1 wherein said culture medium further contains human or animal plasma or serum.

3. The method of claim 1 further comprising, subsequent to the step of culturing, harvesting the human hematopoietic precursor cells from the culture medium.

4. The method of claim 3 wherein the step of harvesting the precursor cells from the culture medium is carried out by centrifugation or filtration of the culture medium.

5. The method of claim 3 further comprising, subsequent to the step of harvesting the precursor cells from the culture medium, resuspending the precursor cells in medium or buffer.

6. The method of claim 1 wherein the step of separating is based upon a physical characteristic associated with the precursor cells and not associated with the mature cells.

7. The method of claim 1 wherein the step of separating is by immunoselection.

8. The method of claim 1 wherein the presence of the CD34 antigen is detected by a procedure selected from the group consisting of flow microfluorimetry, immunofluorescence, immunoperoxidase staining, radioimmunoassay and immunoaffinity chromatography.

9. The method of claim 1 wherein the separation of CD34-positive cells comprises the steps of (a) selecting for CD34-positive cells by exposure to an anti-CD34 antibody; and (b) selecting for HLA-DR-negative/CD34-positive cells by exposure to an anti-HLA-DR antibody.

10. The method of claim 3 further comprising, subsequent to the step of harvesting, fractionating the precursor cells into CD34-positive and CD34-negative populations.

11. The method of claim 10 further comprising, subsequent to the step of fractionating, resuspending the CD34-positive population in a physiologically acceptable medium or buffer.

12. The method of claim 1 wherein the blood product is bone marrow.

13. The method of claim 1 wherein the blood product is umbilical cord blood.

14. The method of claim 1 wherein the blood product is peripheral blood.

15. The method of claim 14 further comprising, prior to the step of separating, administering to the intended donor of the peripheral blood sample a growth factor or drug that increases the number of circulating-hematopoietic precursor cells.

16. The method of claim 15 wherein the growth factor is granulocyte colony stimulating factor or stem cell factor.

17. The method of claim 15 wherein the drug is 5-fluorouracil.

18. The method of claim 1 wherein the precursor cells are cultured under conditions and for a time sufficient to achieve at least an approximately five-fold expansion in the number of precursor cells relative to the initial number of precursor cells present in said blood product.

19. The method of claim 1 wherein the step of separating comprises positive selection of the precursor cells.

20. The method of claim 1 wherein the step of separating comprises negative selection of the precursor cells.

21. The method of claim 1 wherein the step of separating comprises a combination of positive selection and negative selection of the precursor cells.

22. The method of claim 1 wherein the precursor cells are cultured for between four and fourteen days.

23. The method of claim 1 further comprising, prior to the step of separating, preparing a buffy coat from the blood product.

24. The method of claim 1 further comprising, prior to the step of separating, preparing a mononuclear cell fraction from the blood product.

25. The method of claim 1 wherein said precursor cells are inoculated at an initial density of between $1\times10^3$ cells/ml and $1\times10^4$ cells/ml.

26. The method of claim 1 wherein said inoculated separated precursor cells are cultured under conditions sufficient to maintain an oxygen tension of between 3% and 20%.

27. The method of claim 26 wherein the oxygen tension is between 3% and 5%.

28. The method of claim 1 wherein the culture medium further comprises microcarrier beads.

* * * * *